United States Patent [19]
Yoshikumi et al.

[11] 4,159,225
[45] Jun. 26, 1979

[54] METHOD OF PRODUCING A STABLE MONOKARYOTIC MYCELIUM OF *CORIOLUS VERSICOLOR* AND ITS USE IN POLYSACCHARIDE PRODUCTION

[75] Inventors: Chikao Yoshikumi, Kunitachi; Yoshio Omura, Tanashi; Toshihiko Wada, Mibu; Hiromitsu Makita; Takao Ando, both of Tokyo; Noriyuki Toyoda; Kenichi Matsunaga, both of Hino, all of Japan

[73] Assignee: Kureha Kagaku Kogyo Kabushiki Kaisha, Tokyo, Japan

[21] Appl. No.: 826,118

[22] Filed: Aug. 19, 1977

[30] Foreign Application Priority Data

Aug. 30, 1976 [JP] Japan .................................. 51-103379

[51] Int. Cl.$^2$ ...................... C12D 13/04; C12K 1/00; C12B 1/08
[52] U.S. Cl. ................................. 195/31 P; 195/76; 195/81
[58] Field of Search ................. 195/31 P, 81, 104, 53, 195/79, 76

[56] References Cited

U.S. PATENT DOCUMENTS

| 3,759,896 | 9/1973 | Komatsu et al. | 536/1 |
| 3,950,224 | 4/1976 | Ward et al. | 195/76 |
| 4,051,314 | 9/1977 | Ohtsuka et al. | 195/31 P |

OTHER PUBLICATIONS

Alexopoulos, *Introductory Mycology*, John Wiley & Sons, Inc., New York (1952), pp. 339-352.

*Primary Examiner*—Thomas G. Wiseman
*Attorney, Agent, or Firm*—Stevens, Davis, Miller & Mosher

[57] ABSTRACT

When a dikaryotic mycelium of *Coriolus versicolor* (Fr.) Quél. (a species of fungi belonging to the genus Coriolus of Polyporaceae) is subjected to a mechanical treatment such as grinding or shearing in a liquid medium, or when such mycelium is subjected to submerged culture while undergoing mechanical treatment, there is produced a monokaryotic mycelium which is different from the dikaryotic mycelium in morphological and physiological characteristics. The thus obtained monokaryotic mycelium is a novel product and characterized by its extremely high propagation rate as compared with the known dikaryotic mycelium. Also, the substance extracted from the culture of the mycelium has excellent physiological activities.

11 Claims, 4 Drawing Figures

METHOD OF PRODUCING A STABLE MONOKARYOTIC MYCELIUM OF *CORIOLUS VERSICOLOR* AND ITS USE IN POLYSACCHARIDE PRODUCTION

BACKGROUND OF THE INVENTION

This invention relates to a method of producing a novel monokaryotic mycelium from *Coriolus versicolor* (Fr.) Quél. which is a known Basidiomycete belonging to the genus Coriolus of family Polyporaceae.

The usefulness of the polysaccharides obtained from extraction of *Coriolus versicolor* (Fr.) Quél. or culture thereof as a base component for preparation of medical drugs or foods and drinks has become acknowledged recently, and various techniques for producing such Basidiomycete by artificial culture in a high yield have been proposed. Nevertheless, there is not yet available an advantageous method capable of propagating the Basidiomycete in a high yield.

In the course of our study aimed at realizing high-yield propagation of *Coriolus versicolor* (Fr.) Quél., we found that when this Basidiomycete is subjected to submerged culture while performing a mechanical treatment such as grinding or shearing in a liquid medium, the Basidiomycete loses clamp connection, which is its intrinsic morphological characteristic, and is changed into a monokaryotic mycelium, and that the thus formed monokaryotic mycelium is stable and also has a unique characteristic in its extremely high in propagation rate as compared with the known dikaryotic mycelium.

BRIEF SUMMARY OF THE INVENTION

An object of this invention is to provide a method of producing novel monokaryotic mycelia having no clamp connection by performing a mechanical treatment on a known Basidiomycete, *Coriolus versicolor* (Fr.) Quél. composed of dikaryotic mycelium, in a liquid medium or by subjecting such Basidiomycete to submerged culture with mechanical treatment.

Other objects of this invention will become apparent from the following detailed description of the invention.

Figure 1:
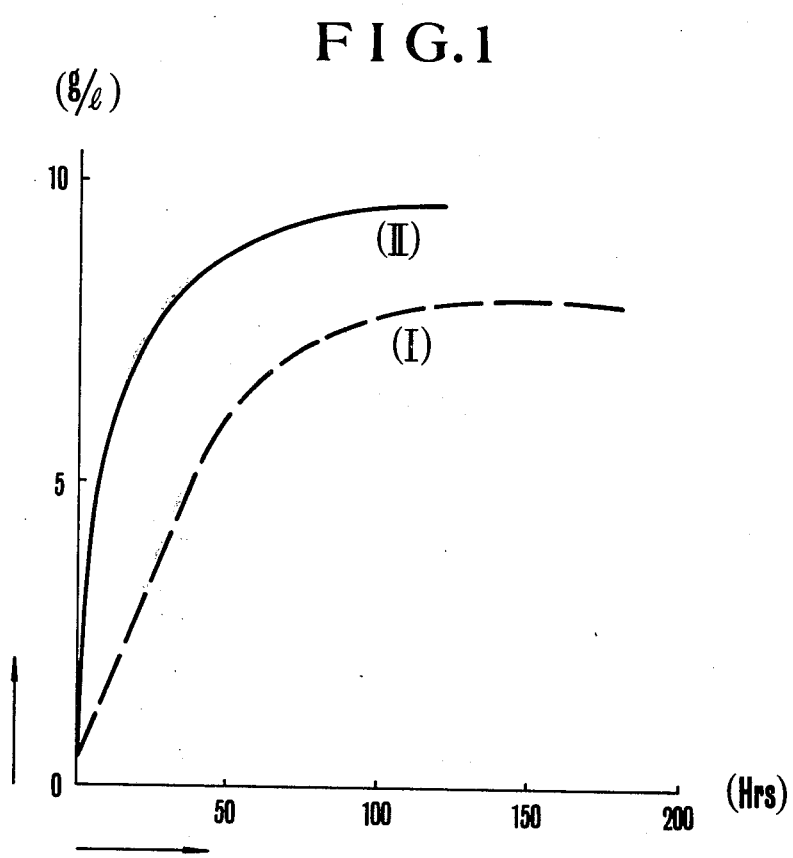
FIG. 1 of the accompanying drawings is a graph showing comparatively a propagation curve for an aerated and agitated culture of the monokaryotic mycelium derived from *Coriolus versicolor* (Fr.) Quél. according to the method of this invention and a similar propagation curve for the known dikaryotic mycelium.

In the graph of FIG. 1, the mycelia concentration (g/l) in the medium is plotted as ordinate and the cultivation time (hr) as abscissa. Also, (I) indicates the propagation curve of the dikaryotic mycelium and (II) the propagation curve of the monokaryotic mycelium.

DETAILED DESCRIPTION OF THE INVENTION

It is generally believed that the fungi constituting a mushroom produce the basidiospores and such spores germinate to form the primary consisting of usually monokaryons, and such mycelia fuse together to form secondary mycelium consisting of the dikaryons. It is said that the monokaryotic mycelium has no ability to form the fruit bodies but the dikaryotic mycelium has such ability. There is available no report concerning generation of the monokaryotic mycelium from the spores in *Coriolus versicolor* (Fr.) Quél. Moreover, the white aerial mycelium obtained in our experiments by cultivating the spores was dikaryotic, and this appears to be due to the fact that the monokaryotic mycelium from the spores is rapidly converted into dikaryotic.

The monokaryotic mycelium obtained from the dikaryotic mycelium according to this invention can be maintained stably, presenting a striking difference from the existing dikaryotic mycelium. Table I below lists the differences between the monokaryotic mycelium of *Coriolus versicolor* (Fr.) Quél. according to this invention and the dikaryotic mycelium.

Table 1

| Items | Dikaryotic mycelium | Monokaryotic mycelium (this invention) |
|---|---|---|
| Appearance | | |
| 1. Submerged culture | Non-suspended condition. | Suspended condition. |
| 2. Plate culture | Aerial mycelium is formed. | Not formed. |
| Microscopic observation | | |
| 3. Formation of clamp connection | Observed. | None. |
| 4. Shape of mycelium | Long and fine. | Shorter and far thicker than dikaryotic mycelium. |
| Physiological and biochemical properties | | |
| 5. Propagating rate | Low. | High. |
| 6. Cellulose assimilation | Positive. | Slightly positive. |
| 7. Potassium nitrate as a sole nitrogen source | No growth. | Growth. |
| 8. Thiamine | Required. | Not required. |
| 9. Litmus milk medium | Acidified. | Not acidified. |

The following facts are to be further noted in connection with the properties of the respective mycelia shown in the above table. The ordinary dikaryotic mycelia obtained by cultivation of *Coriolus versicolor* (Fr.) Quél. according to a conventional method are usually in the form of pellets. On the other hand, the monokaryotic mycelia, when cultivated, are not formed into pellets and the culture assumes a turbid condition as if pulp were suspended in water, thus presenting an obvious difference from the ordinary dikaryotic mycelia. The method for counting nuclei in the cell was used for the first time by the present inventors, and this method comprises the following means and techniques.

Helly's fixing fluid is first added to the Basidiomycete mycelia, and then the mycelia are allowed to stand for usually about 24 hours and then washed with water until decolored. The thus obtained mycelia are immersed in 1 - N hydrochloric acid solution and the solution is heated to a temperature of 60° C. After cooling to room temperature and washing with water, they are further immersed in 20 to 50 times diluted nitric acid solution, followed by additional washing with water. The period of immersion is from ten to twenty minutes in the hydrochloric acid solution and a few minutes in the nitric acid solution. The thus obtained fibrous cells are spread on a slide glass and left thereon until moisture evaporates away, and then Giemsa's solution is added dropwise thereto. At the point when staining has been accomplished by the solution (approximately 10 minutes later), the cells are washed lightly with water and then dried. After drying, the cells are examined under a light microscope of 1,000 magnifications and the circular red-stained spots (considered as nuclei) are counted. Thus, the number of nuclei can be determined by counting the red-stained spots in one cell.

"Helly's fixing fluid" used herein is a solution of which the base is prepared by dissolving 2.5 gr of potassium bichromate, 1 gr of sodium sulfate and 5 gr of mercuric chloride in 100 ml of water, and immediately before use, such base solution is mixed with formalin in an amount of 5 ml per 100 ml of the solution.

"Giemsa's solution" is a nucleus staining solution prepared by dissolving 3.0 gr of azur II eosine and 0.8 gr of azur in 250 ml of glycerin by heating them to 60° C., further adding thereto 250 ml of methyl alcohol, allowing the mixed solution to stand for 24 hours and then filtering the solution. In use, the thus prepared stock solution is diluted by adding a phosphoric acid buffer solution (pH 6.4-6.8) in an amount of 100 ml for 3 ml of the stock solution.

As a result of the measurements by the above-described method, it was found that the number of nuclei in one cell of the ordinary pellet-shaped mycelium is 2 whereas that of the suspension-type mycelium according to this invention is 1.

The monokaryotic mycelium exhibiting the peculiar properties such as stated above can be produced according to this invention by subjecting the dikaryotic mycelium of *Coriolus versicolor* (Fr.) Quél. to a mechanical (physical) treatment such as grinding or shearing in a liquid medium, or by subjecting the dikaryotic mycelium to submerged culture while mechanical treating the mycelium. More specifically, this method may be accomplished in the following ways.

(1) In case of subjecting the dikaryotic mycelium of *Coriolus versicolor* (Fr.) Quél. to shaking culture, the mycelium is ground by adding inert solid granular materials such as glass beads.

(2) In case of subjecting the dikaryotic mycelium to continuous submerged culture, such culture is performed while shearing the mycelium with an agitating element.

(3) In case of subjecting the dikaryotic mycelium to submerged culture, the mycelium is sheared or ground by a homogenizer to such an extent that no pellet-shaped mycelium is noted by external observation.

In the formation of the monokaryotic mycelium under the above-mentioned conditions, it is preferable to apply additionally the following techniques.

(i) An enriched nutritious condition is provided by using a medium with 1.5 to 3 times as high concentration as the ordinary medium, for example, a glucose-yeast extract medium containing 5% glucose and 0.75% yeast extract.

(ii) The atmosphere of submerged culture is maintained under reduced oxygen partial pressure. The "reduced oxygen partial pressure" may be provided by keeping the fermenter airtight, or by flowing an inert gas such as nitrogen gas or carbon dioxide gas into the fermenter.

(iii) Submerged culture is carried out continuously while additionally supplying the liquid medium.

The dikaryotic mycelium of *Coriolus versicolor* (Fr). Quél. can be easily converted into the monokaryotic mycelium by employing the above-mentioned methods (1)-(3) either singly or in suitable combination with the techniques (i)-(iii). In case a sufficient amount of monokaryotic mycelia can not be obtained by one run of culture, the above-mentioned operation is continued after homogenizing the culture until the desired amount of monokaryotic mycelia is obtained. Culture is usually practiced at a temperature of $25\pm5°$ C. for a period of 3 to 15 days.

It was found that the monokaryotic mycelia of *Coriolus versicolor* (Fr.) Quél. obtained according to the method of this invention always maintain the same state and same properties if cultivation is continued under the above-mentioned conditions for production of monokaryotic myeclia. This means that the monokaryotic mycelium obtained according to the method of this invention comes out as the same monokaryotic mycelium in the next generation, maintaining the properties of monokaryotic mycelia shown in Table 1.

In plate culture or surface culture (stationary culture) of the monokaryotic mycelium, it is undesirable to form aerial mycelia, but aerial mycelia are produced if cultivation is continued for several months. These aerial mycelia are dikaryotic, and when it is inoculated into bed log to form fruit bodies, they proved to be *Coriolus versicolor* (Fr.) Quél. itself. This revealed that the mycelium produced is the same as the original one.

These facts indicate that the monokaryotic mycelium of *Coriolus veriscolor* (Fr.) Quél. according to this invention is derived from the original dikaryotic mycelium of *Coriolus versicolor* (Fr.) Quél.

The monokaryotic mycelium of this invention is a novel mycelium which was developed for the first time by the method of this invention, and this novel mycelium was named *Coriolus versicolor* (Fr.) Quél. GX-101-3 and deposited under FERM-P No. 3686 on Aug. 25, 1976 in the Fermentation Research Institute, Agency of Industrial Science and Technology (Chiba-shi, Japan), a Japanese governmental organ.

The characteristic features of the monokaryotic mycelium of *Coriolus versicolor* (Fr.) Quél. according to this invention are as shown in Table 1, but the greatest industrial significance of this fungus is its high rate of propagation. The propagation rate of this fungus is 1.5 to 10 times as high as those of the original dikaryotic mycelium, and obviously, such a high propagation rate is extremely beneficial for industrial production.

This monokaryotic mycelium can be applied for the same purposes of use as the dikaryotic mycelium of *Coriolus versicolor* (Fr.) Quél. For instance, it is possible to obtain nitrogen-containing polysaccharide from its extraction with an aqueous medium (such as water, dilute alkaline solution or dilute acid solution), and such nitrogen-containing polysaccharide can be used for preparation of a pharmaceutical preparation having utility as an anti-tumour agent, immunity activating agent, antiviral drug, antifungal agent, anti-leprous drug, appetite promoting drug, etc.

It is also possible to collect various types of enzymes such as protease, amylase, etc., by low-temperature extraction. Further, the mycelium itself or its extracts or residues can be used for foods and drinks, feed for animals and fertilizer for plants.

Beside the above-mentioned utilities, the mycelium of this invention can be employed for all the uses of *Coriolus versicolor* (Fr.) Quél.

This invention is now described in further detail by way of several preferred embodiments, but these embodiments are not to be construed as restricting the scope of this invention. In the following examples percent (%) is by weight unless otherwise noted.

EXAMPLE 1

Production of monokaryotic mycelium 100 ml of a liquid medium containing 5% of glucose (produced by Showa Sangyo Co., Ltd.) and 0.75% of yeast extract (produced by Kyokuto Seiyaku Kogyo Co., Ltd.) was pipetted into a 500-ml conical flask, and after b 20-minute steam sterilization at 120° C. in an autoclave, the medium was inoculated with 1 ml of a suspension of mycelia prepared by dispersing the mycelia of *Coriolus versicolor* (Fr.) Quél. (obtained from 20-day stationary culture at 25° C. by using 50 ml liquid medium containing 3% of glucose and 0.5% of yeast extract in 60 ml of physiological saline solution by breaking up the mycelial mat with a blender at speed of 6,000 r.p.m. for 3 minutes), and then shaking culture was started at a speed of 200 r.p.m. at 25° C. 3 days after start of cultivation, the cultivated material was transferred aseptically into a 200-ml blender cup (mfd. by Sakuma Seisakujo), and after grinding the material by a homomixer (mfd. by Sakuma Seisakujo) at a speed of 10,000 r.p.m. for 10 minutes, shaking culture was immediately resumed for a total shaking culture period of 7 days. The thus cultivated mycelium had no clamp connection and showed little generation of aerial mycelia in a standard agar plate medium. The result of the microscopic examination after staining described below showed that the obtained mycelia were all monokaryotic.

Staining 1 ml of the broth containing the mycelia obtained in the manner described above is mixed with 10 ml of water and then subjected to centrifugal separation at 2,000 to 5,000 G for 5 minutes. The supernatant liquid is eliminated and the mycelia are transferred into a test tube, to which Helly's fixing fluid is added. After 24-hour standing, the separated cells are washed with 10 ml of water until they are decolored. Then the cells are put into 10 ml of 1N hydrochloric acid and heated at 60° C. for 15 minutes, followed by cooling to room temperature, washing with 10 ml of water, 2-minute immersion in 10 ml of 20 to 50 times diluted nitric acid solution and 2 to 3 washings with 10 ml of water.

The obtained fibrous cells are spread on a slide glass to let moisture evaporate away and then a few drops of Giemsa's solution are added onto the cells, and after 15-minute standing, they are washed lightly with water and then dried.

When the thus nucleus-stained cell is examined under a microscope of 1,000 magnification, each nucleus is observed as a circular red-stained spot. Therefore, the number of nuclei can be easily determined by counting the circular red-stained spots in one cell of the mycelium. The obtained mycelium could not acidify litmus milk and had no gelatin-liquefying ability.

Propagation of monokaryotic mycelium

The monokaryotic mycelia obtained in the way described above was fed with 12 liters of a liquid medium containing 5% of glucose and 0.75% of yeast extract into a 20-liter jar fermenter (mfd. by Kyoritsu Riko Co., Ltd.), followed by blowing 2 kg/cm$^2$ of steam directly into the jar fermenter. After steam sterilization at 120° C. for 20 minutes and cooling, 1 liter of suspension containing the monokaryotic mycelia was inoculated (at the rate of 0.5 g/l), immediately followed by cultivation at aeration rate of 0.5 v.v.m. and agitating speed of 550 r.p.m. For sake of comparison, cultivation of the dikaryotic mycelium was carried out under completely identical conditions as those used for cultivation of the monokaryotic mycelium. When the propagation rates of these mono- and dikaryotic mycelia are compared by way of the time required for attaining the mycelia concentration of 8 g/l, it is noted that the monokaryotic mycelium requires only ¼ of the cultivation time required by the dikaryotic mycelium (see FIG. 1). It was also confirmed that the propagation yield of the monokaryotic mycelium increased about 20% over that of the dikaryotic mycelium.

EXAMPLE 2

Figure 2:
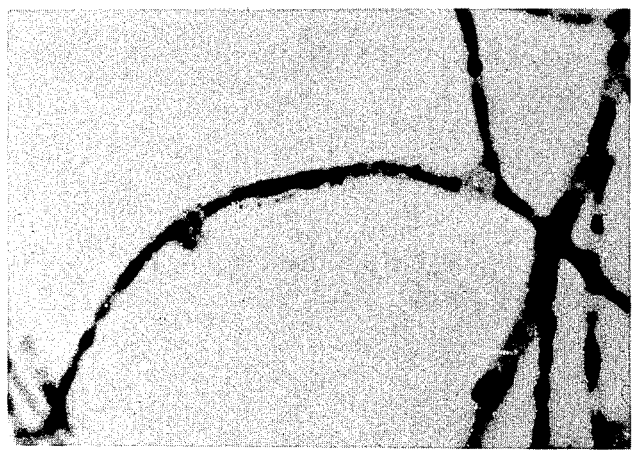
FIGS. 2 and 4 are microphotographs of the dikaryotic mycelia obtained from slant culture of *Coriolus versicolor* (Fr.) Quél.

Calculation of the number of nuclei was made, after the manner of Example 1, on the mycelium obtained form slant culture of *Coriolus versicolor* (Fr.) Quél. As a result, it was found that, as shown in the photograph of FIG. 2, all of these cells are dikaryotic and no monokaryotic mycelium was detected.

This original fungus is named *Coriolus versicolor* (Fr.) Quél. CM-101 and deposited under FERM-P No. 2412 on December 25, 1973 in the afore-mentioned governmental depository.

100 ml of a liquid medium containing 5% of glucose and 0.75% of yeast extract was put into a 500-ml conical flask and sterilized therein by heating. This medium was then inoculated with the above-described dikaryotic mycelium by using a platinum loop and subjected to 3-day shaking culture (preculture) in a room adjusted to a temperature of 25°±2° C. There were consequently produced pellet-shaped mycelia. The broth containing these pellet-shaped mycelia was homogenized by a homo-blender (mfd. by Sakuma Seisakujo) for 5 minutes and then subjected to a shearing treatment, whereby the pellet form substantially disappeared. Cultivation was continued under the above-mentioned conditions, and 4 days later (main culture), the pellet-shaped mycelia were again homogenized for 5 minutes and then subjected to a shearing treatment. The concentration of cells of the fungus at this stage was 11 g/l.

1 ml of broth containing the homogenized mycelia was added to the same liquid medium as used in the first run of cultivation and then subjected to the second run of cultivation under the same conditions as in the first run. However, the cultivation period was slightly changed, that is, the preculture was performed for 3 days and the main culture also for 3 days. The fungal cell concentration was of the substantially same level as in the first run of shaking culture.

The third run of cultivation was further continued in the similar manner, with a fungal cell concentration reaching the substantially same level as that of the first run of shaking culture by 2 days of preculture and 3 days of main culture.

Likewise, a fourth run of cultivation was carried out, obtaining a broth with a fungal cell concentration of 12 g/l, higher than that of the first run of cultivation, by 2-day preculture and 2-day main culture. The obtained mycelia were not in the form of pellets and stayed dispersed in the form of pulp, requiring no homogenization treatment.

The fungal cells, as observed by a microscope, had no clamp connection which is found in the ordinary dikaryotic mycelium, and each was about twice as large in width as the dikaryotic mycelium.

Figure 3:
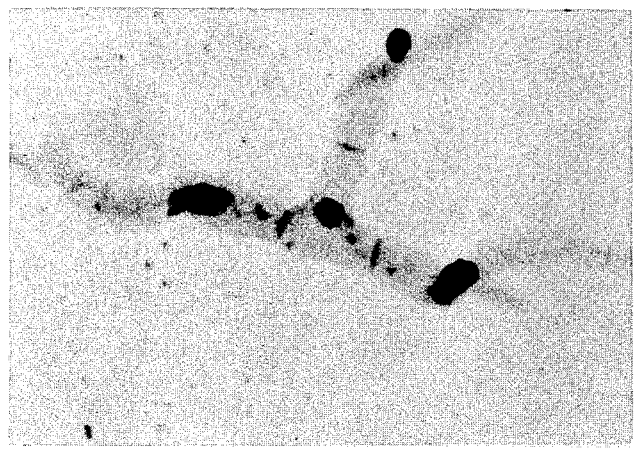
FIG. 3 is a microphotograph of the monokaryotic mycelia obtained according to the present invention.

From the measurement of the number of nuclei by the method described in Example 1, it was ascertained that these cells are all monokaryotic mycelia as shown in a microphotograph of FIG. 3.

When the mycelia were further cultivated under the same conditions as in the previous run of cultivation, the propagated mycelia were derived from the monokaryotic mycelia and had all of the properties possessed by the monokaryotic mycelia shown in Table 1.

It was also found that the monokaryotic mycelium was more than twice as high in propagation rate as the dikaryotic mycelium.

10 gr of the dried product of the monokaryotic mycelium obtained in the above-described method was extracted with 300 ml of hot water at 95° to 100° C. for 3 hours. The extract solution was concentrated under reduced pressure to 30° C. and then mixed with pure ethanol to provide a concentration of 90%, and the produced precipitate was dried, giving 0.2 gr of gray powder.

A chemical analysis of this gray powder revealed that this substance was a nitrogen-containing high-molecular-weight polysaccharide. When this substance was administered to mice having transplanted Sarcoma-180 of the solid type, it demonstrated a high anti-tumor activity.

EXAMPLE 3

100 ml of a liquid medium containing 5% of glucose and 0.75% of yeast extract was fed into a 500-ml-capacity conical flask which already contained 8 gr of glass beads with diameter of 2 to 5 mm, and this mixed medium, after heat sterilization, was inoculated with the dikaryotic mycelium of *Coriolus versicolor* (Fr.) Quél., same as employed in Example 1, by using a platinum loop and then subjected to 7-day shaking culture at 25°±2° C.

1 ml of broth containing the thus obtained mycelium was supplied to a medium containing glass beads identical to that mentioned above and further subjected to a second 6-day shaking culture.

The resultant product was further subjected to a third run of shaking culture for a period of 5 days.

The thus produced mycelium had no clamp connection and was about 1.5 times as large in width as the original dikaryotic mycelium, and the result of counting nuclei in the manner of Example 1 revealed that it a monokaryotic mycelium.

1 ml of this broth was inoculated into 100 ml of a liquid medium containing 5% of glucose and 0.75% of yeast extract and not containing any glass beads and cultivated at 25°±2° C. The mycelia concentration 3 days after start of cultivation was 10.5 g/l, while the result of similar culture of the dikaryotic mycelium showed 7 g/l concentration 4 days after start of cultivation.

EXAMPLE 4

100 ml of a liquid medium containing 5% of glucose and 0.75% of yeast extract was put into a 500-ml conical flask, and this medium, after heat sterilization, was inoculated with the dikaryotic mycelium of *Coriolus versicolor* (Fr.) Quél. same as employed in Example 1 by using a platinum loop and then subjected to shaking culture for 3 days. After a homogenization treatment, the entirety of the fermenter was covered by a polyethylene bag and sealed from the external air, followed by 4-day cultivation.

At the point of completion of the cultivation, 5.0% of $CO_2$ gas was contained in the fermenter atmosphere.

1 ml of broth containing the thus produced mycelium was inoculated into the medium in the manner of the first run of cultivation and then subjected to the second run of shaking culture in the same way as the first run. Such cultivation was further repeated twice. As the result of measurement as conducted in Example 1, it was ascertained that the mycelia produced in this process of cultivation were all monokaryotic.

EXAMPLE 5

Figure 4:
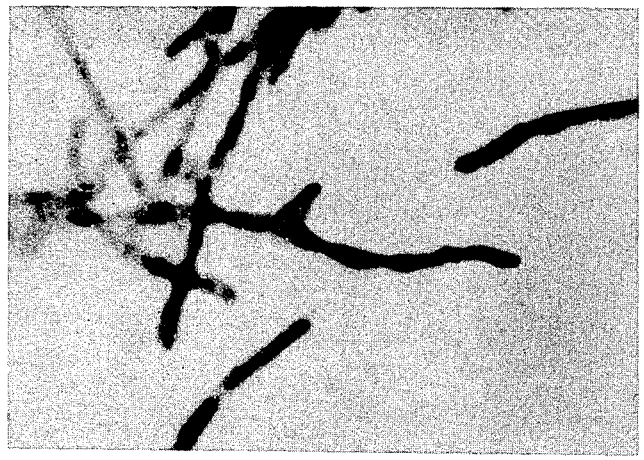

A sample of the mycelia obtained from slant culture of *Coriolus versicolor* (Fr.) Quél. was subjected to the nuclei count procedure described in Example 1, whereby it was ascertained that all of the mycelia were dikaryotic and no monokaryotic mycelium was present as seen in the photograph of FIG. 4. This indicates that the mycelium obtained from this run of cultivation is dikaryotic mycelium.

This fungus is *Coriolus versicolor* (Fr.) Quél. CM-103 and deposited under FERM-P No. 2414 on December 25, 1973 in the afore-mentioned governmental depository.

100 ml of a liquid medium containing 5% of glucose and 0.75% of yeast extract was put into a 500-ml-capacity conical flask and, after heat sterilization, inoculated with the mycelium of the *Coriolus versicolor* (Fr.) Quél. CM-103 by using a platinum loop, followed by 7-day shaking culture at 25°±2° C. The mycelia in this culture were dikaryotic and contained in a concentration of 10.8 g/l.

The thus obtained dikaryotic mycelia were inoculated in the concentration of 0.01% into 20 liters of a liquid medium having dissolved therein 10% of glucose and 1.5% of yeast extract and subjected to submerged culture under agitation in a fermenter adjusted to 25°±2° C. by using a paddle type agitator at the speed of 500 r.p.m. After 7-day cultivation, the mycelia constituted a concentration of 10.2 g/l in the broth. 20 ml of this broth was inoculated into the same medium and the second run of cultivation was performed under the same conditions for 6 days. Similar cultivation was further repeated for 5 days in the third run and for 4 days in the fourth run.

After completion of the fourth run of cultivation, the broth was in the form of uniform pulp and contained the produced mycelia in a concentration of 11.5 g/l. The mycelia had no clamp connection and were all monokaryotic mycelia.

What is claimed is:

1. A method of producing a monokaryotic mycelium of *Coriolus versicolor* (Fr.) Quél., comprising shearing or grinding dikaryotic mycelia of *Coriolus versicolor* (Fr.) Quél. in a liquid medium and subsequently or simultaneously cultivating the mycelia in a submerged culture and recovering the monokaryotic mycelium having a higher probagation rate than the dikaryotic mycelia.

2. The method according to claim 1, wherein said shearing or grinding is by a homogenizer.

3. The method according to claim 1, wherein said mechanical treatment is shearing or grinding by an agitator.

4. The method according to claim 1, wherein said submerged culture is carried out continuously while additionally supplying the liquid medium.

5. The method according to claim 1 wherein said dikaryotic mycelia are ground using an inactive solid granular material.

6. The method according to claim 5, wherein said inert solid granular materials are glass beads.

7. The method according to claim 1, wherein said submerged culture is carried out by successive inoculation of a plurality of mediums.

8. The method according to claim 1 wherein said submerged culture is in a medium containing 5–10% weight glucose and 0.75–1.5% by weight yeast extract.

9. The method of claim 1 wherein said cultivating of said submerged culture is conducted in an air-tight fermentor or in a nitrogen or carbon dioxide atmosphere.

10. The method of claim 1 wherein said monokaryotic mycelia are of the strain GX-101-3 of *Coriolus versicolor* (Fr.) Quèl., deposited under FERM-. No. 3686 in the Fermentation Research Institute of the Agency of Industrial Science and Technology of the Japanese Government.

11. A process for producing a polysaccharide comprising contacting the mycelia produced according to claim 1 with an aqueous solution to extract the nitrogen-containing polysaccharide and separating the extracted polysaccharide from the aqueous solution.

* * * * *